United States Patent
Aubourg et al.

(10) Patent No.: US 10,801,040 B2
(45) Date of Patent: Oct. 13, 2020

(54) METHODS AND PHARMACEUTICAL COMPOSITIONS FOR EXPRESSING A POLYNUCLEOTIDE OF INTEREST IN THE PERIPHERAL NERVOUS SYSTEM OF A SUBJECT

(71) Applicants: INSERM (INSTITUT NATIONAL DE LA SANTÉ ET DE LA RECHERCHE MÉDICALE), Paris (FR); UNIVERSITE PARIS-SUD, Orsay (FR); COMMISSARIAT À L'ÉNERGIE ATOMIQUE ET AUX ÉNERGIES ALTERNATIVES, Paris (FR); ASSISTANCE PUBLIQUE-HÔPITAUX DE PARIS (APHP), Paris (FR); UNIVERSITÉ DE MONTPELLIER, Montpellier (FR)

(72) Inventors: Patrick Aubourg, Le Kremlin Bicêtre (FR); Nicolas Tricaud, Montpellier (FR); Benoît Gautier, Le Kremlin Bicêtre (FR)

(73) Assignees: INSERM (INSTITUT NATIONAL DE LA SANTÉ ET DE LA RECHERCHE MÉDICALE), Paris (FR); UNIVERSITE PARIS-SUD, Orsay (FR); COMMISSARIAT À L'ÉNERGIE ATOMIQUE ET AUX ÉNERGIES ALTERNATIVES, Paris (FR); ASSISTANCE PUBLIQUE-HÔPITAUX DE PARIS (APHP), Paris (FR); UNIVERSITÉ DE MONTPELLIER, Montpellier (FR)

( * ) Notice: Subject to any disclaimer, the term of this patent is extended or adjusted under 35 U.S.C. 154(b) by 194 days.

(21) Appl. No.: 15/740,036

(22) PCT Filed: Jul. 6, 2016

(86) PCT No.: PCT/EP2016/066014
§ 371 (c)(1),
(2) Date: Dec. 27, 2017

(87) PCT Pub. No.: WO2017/005806
PCT Pub. Date: Jan. 12, 2017

(65) Prior Publication Data
US 2018/0187212 A1    Jul. 5, 2018

(30) Foreign Application Priority Data
Jul. 7, 2015 (EP) ................... 15306111

(51) Int. Cl.
*A01N 63/00* (2020.01)
*A61K 48/00* (2006.01)
*C12N 15/86* (2006.01)
*A61K 35/761* (2015.01)
*C12N 15/113* (2010.01)
*A61K 39/00* (2006.01)

(52) U.S. Cl.
CPC ............ *C12N 15/86* (2013.01); *A61K 35/761* (2013.01); *C12N 15/113* (2013.01); *A61K 48/00* (2013.01); *A61K 2039/525* (2013.01); *C12N 2310/11* (2013.01); *C12N 2310/14* (2013.01); *C12N 2750/14143* (2013.01); *C12N 2750/14171* (2013.01)

(58) Field of Classification Search
CPC .. C12N 15/86; C12N 15/113; C12N 2310/11; C12N 2310/14; C12N 2750/14171; C12N 2750/14143; A61K 35/761; A61K 2039/525; A61K 48/00
See application file for complete search history.

(56) References Cited

U.S. PATENT DOCUMENTS

| 2009/0017039 A1* | 1/2009 | Mi ........................ C07K 16/18 424/152.1 |
| 2013/0039888 A1 | 2/2013 | McCarty et al. |
| 2013/0225666 A1 | 8/2013 | Kaspar et al. |

FOREIGN PATENT DOCUMENTS

WO    2011/133890 A1    10/2011

OTHER PUBLICATIONS

Hirai (2012, Human Gene Therapy Methods, 23:119-127).*
Hirai B (2014, Molecular Therapy, 22:409-419).*
Gonzalez (Apr. 2014, Nature Protocols, 9:1160-1169).*
C N Mattar et al: "Systemic delivery of scAAV9 in fetal macaques facilities neuronal transduction of the central and peripheral nervous systems", Gene Therapy, vol. 20, No. 1, Jan. 1, 2013, pp. 69-83.
Mai K. Elmallah et al: "Retrograde Gene Delivery to Hypoglossal Motonuerons Using Adeno-Associated Virus Serotype 9", Human Gene Therapy Methods, vol. 23, No. 2 Apr. 1, 2012, pp. 148-156.

(Continued)

*Primary Examiner* — Valarie E Bertoglio
(74) *Attorney, Agent, or Firm* — W&C IP

(57) ABSTRACT

The present invention relates to methods and pharmaceutical compositions for expressing a polynucleotide of interest in the peripheral nervous system of a subject. In particular, the present invention relates to a method for selectively expressing a polynucleotide of interest in the peripheral nervous system of a subject in need thereof comprising the step of transducing a peripheral nerve of the subject with an amount of an AVV9 vector containing the polynucleotide of interest.

10 Claims, 2 Drawing Sheets

(56) References Cited

OTHER PUBLICATIONS

Figure 1:
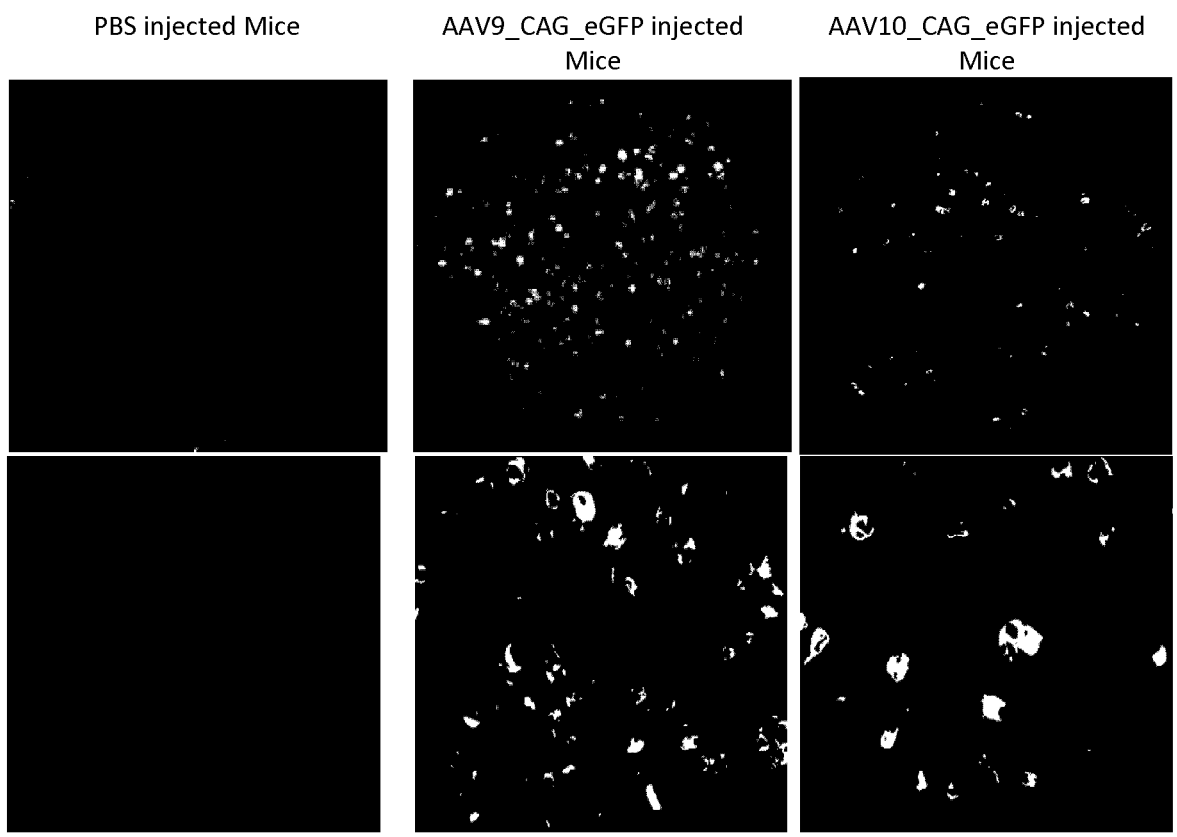

J Horns et al: "Schwann cell targetting via intrasciatic injection of AAV8 as gene therapy strategy for peripheral nerve regeneration", Gene Therapy, vol. 18, No. 6, Feb. 17, 2011, pp. 622-630.
Boulis Nicholas M et al: "Adeno-associated viral vector gene expression in the adult rat spinal cord following remote vector delivery", Neurobiology of Disease, Blackwell Scientific Publications, Oxford, GB, vol. 14, No. 3, Dec. 1, 2003, pp. 535-541.

* cited by examiner

| Region of the sciatic nerve | Oct-embedded sciatic nerve cryosections | Paraffin-embedded sciatic nerve sections | % of myelinating Schwann cells Mean (%) | SD (%) |
|---|---|---|---|---|
| 5cm proximal from the injection site | | | 0 | 0 |
| 3.5cm proximal from the injection site | | | 20 | 1 |
| 2cm proximal from the injection site | | | 55 | 1 |
| Injection site | | | 68 | 1 |
| 1.5cm distal from the injection site | | | 70 | 1 |

Figure 2

METHODS AND PHARMACEUTICAL COMPOSITIONS FOR EXPRESSING A POLYNUCLEOTIDE OF INTEREST IN THE PERIPHERAL NERVOUS SYSTEM OF A SUBJECT

FIELD OF THE INVENTION

The present invention relates to methods and pharmaceutical compositions for expressing a polynucleotide of interest in the peripheral nervous system of a subject.

BACKGROUND OF THE INVENTION

Efficient gene transfer to the peripheral nervous system (PNS) is critical for gene therapy of inherited and acquired peripheral neuropathies, accelerating peripheral nerve regeneration or pain treatment. The PNS contains different cell types, mostly postmitotic, and their continuous communication is essential for the accurate function of the whole system. For instance, myelination of the peripheral axons involves reciprocal interactions between Schwann cells and neurons. In this context, expression of a polynucleotide of interest by the appropriate cell type may be crucial to maintain or enhance both, the crosstalk between different cell types and the PNS function. In particular, specific transduction of non-neuronal cell types in the PNS, particularly of Schwann cells, may be of great interest for the treatment of demyelinating diseases. Specific cell targeting can be achieved by using different viral vectors that can enter a particular cell type through its specific receptor. Different serotypes of adeno-associated vectors (AAV) also transduce sensory neurons in the dorsal root ganglia (DRG) through direct administration into the cerebral spinal fluid or via retrograde transport. Recently it has been shown that AAV8-driven expression of ciliary neurotrophic factor (CNTF) by mouse Schwann cells increases the expression of myelin protein and improves regeneration of injured sciatic nerve shortly after in vivo transduction (Homs J, Ariza L, Pagès G, Udina E, Navarro X, Chillón M, Bosch A. Gene Ther. 2011 June; 18(6):622-30).

SUMMARY OF THE INVENTION

The present invention relates to methods and pharmaceutical compositions for expressing a polynucleotide of interest in the peripheral nervous system of a subject. In particular, the present invention is defined by the claims.

DETAILED DESCRIPTION OF THE INVENTION

The inventors have investigated the intrasciatic injection of AAV9 in mice and non-human primate. They showed a strong transduction rate of myelinated Schwann cells with a good diffusion of the vector, never obtained and described in the literature up to now. Accordingly these results highlight that AAV9 and AVV10 vectors could represent a useful therapeutic tool to express a polynucleotide of interest in myelinated Schwann cells in pathologies affecting the peripheral nervous system.

Thus a first object of the present invention relates to a method for selectively expressing a polynucleotide of interest in the peripheral nervous system of a subject in need thereof comprising the step of transducing a peripheral nerve of the subject with an amount of an AAV9 vector containing the polynucleotide of interest.

As used herein, the term "subject" refers to a human or another mammal (e.g., mouse, rat, rabbit, hamster, dog, cat, cattle, swine, sheep, horse or primate). In some embodiments, the subject is a human being.

Typically the subject is affected or likely to be affected with a disease affecting the peripheral nervous system. Accordingly a wide variety of diseases may thus be treated given the teachings provided herein and typically include peripheral demyelinating diseases. In particular, the method of the present invention is particularly suitable for selectively expressing the polynucleotide of interest in axons. More particularly, the method of the present invention is particularly suitable for selectively expressing the polynucleotide of interest in Schwann cells. The method of the present invention has thus wide applicability to the treatment of peripheral demyelinating diseases affecting the functions of peripheral ganglionic neurons, sympathetic, sensory neurons, and motor neurons. In particular, the method of the present invention is useful in treatments designed to rescue, for example, retinal ganglia, inner ear and acoustical neurons, and motor neurons. In particular, the method of the present invention is particularly suitable for preventing peripheral nerve demyelination. The wide variety of defects exhibited in peripheral nerves affected by peripheral demyelinating diseases can each be uniquely attributed to an equally wide variety of causes. For instance, peripheral demyelinating diseases can be genetically acquired ("hereditary peripheral demyelinating diseases"), or can result from a systemic disease, or can be induced by a toxic agent or an infectious agent ("acquired peripheral demyelinating diseases").

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the method of the present invention is suitable for the treatment of hereditary peripheral demyelinating diseases. Hereditary peripheral demyelinating diseases are caused by genetic abnormalities which are transmitted from generation to generation. For several of these, the genetic defect is known, and tests are available for diagnosis and prenatal counseling. In particular, the diagnosis of a hereditary peripheral demyelinating disease is usually suggested with the early onset of neuropathic symptoms, especially when a positive family history is also present. Prior to the recent genetic advances, the diagnosis was supported by typical findings of marked slowing of the nerve conduction studies on electromyography and a nerve biopsy. Typical findings on a nerve biopsy include the presence of so-called onion-bulbs, indicating a recurring demyelinating and remyelinating of the nerve fibers. There are a number of hereditary demyelinating neuropathies. Examples include but are not limited to Refsum's disease, Abetalipoproteinemia, Tangier disease, Krabbe's disease, Metachromatic leukodystrophy, Fabry's disease, Dejerine-Sottas syndrome, —and others. Of all the hereditary peripheral demyelinating diseases, the most common by far is Charcot-Marie-Tooth Diseases. Charcot-Marie-Tooth (CMT) Diseases are the most common hereditary neurological disorders. It is characterized by weakness and atrophy of muscles due to demyelination of peripheral nerves and associated degeneration of axons and anterior horn cells. During the last 15 years, there has been a substantive increase in knowledge about the genetic basis of Charcot-Marie-Tooth disease (CMT) with over 60 genes known at present. A regularly updated list can be found at http://www.molgen.ua.ac.be/CMTMutations/Home/IPN.cfm. Autosomal dominant inheritance is usual, and associated degenerative CNS disorders, such as Friedreich's ataxia, are common. In some embodiments, the method of the present invention can be used for the treatment of Charcot-Marie-Tooth disease type 4F and Charcot-Marie-Tooth disease due to duplication or deletion of the PMP22 gene. In some embodiments, the method of the present invention can be used in the treatment of Familial Amyloidotic Neuropathy and other related hereditary peripheral demyelinating diseases. The method of the present invention can be used in the treatment of hereditary porphyria, which can have components of peripheral neuropathy. Still another hereditary peripheral demyelinating disease for which the method of the present inventions can be used for treatment is hereditary sensory neuropathy Type II (HSN II). In some embodiments, the method of the present invent can be used for the treatment of certain muscular dystrophies.

The method of the present invention is also suitable for the treatment of acquired peripheral demyelinating diseases.

In some embodiments, the method of the present invention is suitable for the treatment of diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex which causes weakness in one or more nerves, or lumbosacral plexopathy or amyotrophy which causes weakness in the legs.

In some embodiments, the method of the present invention can also be used in the treatment of immune-mediated neuropathies. The main function of the immune system is to protect the body against infectious organisms which enter from outside. In some cases, however the immune system turns against the body and causes autoimmune disease. The immune system consists of several types of white blood cells, including T-lymphocytes, which also regulate the immune response; and B-lymphocytes or plasma cells, which secrete specialized proteins called "antibodies". Sometimes, for unknown reasons, the immune system mistakenly attacks parts of the body such as the peripheral nerves. This is "autoimmune" Peripheral Neuropathy. There are several different types, depending on the part of the peripheral nerve which is attacked and the type of the immune reaction. For instance, the method of the present invention is suitable for treating Guillain-Barre Syndrome (GBS). GBS is an acute neuropathy because it comes on suddenly or rapidly. Guillain-Bane Syndrome can progress to paralysis and respiratory failure within days or weeks after onset. The neuropathy is caused when the immune system destroys the myelin sheaths of the motor and sensory nerves. It is often preceded by infection, vaccination or trauma, and that is thought to be what triggers the autoimmune reaction. The disease is self-limiting, with spontaneous recovery within six to eight weeks. But the recovery is often incomplete.

Other acquired peripheral demyelinating diseases which begin acutely, and which can be treated by the method of the present invention, include Acute Motor Neuropathy, Acute Sensory Neuropathy, and Acute Autonomic Neuropathy, in which there is an immune attack against the motor, sensory or autonomic nerves, respectively. The Miller-Fisher Syndrome is another variant in which there is paralysis of eye gaze, incoordination, and unsteady gait Still another acquired peripheral demyelinating disease which is may be treated by the method of the present invention is Chronic Inflammatory Demyelinating Polyneuropathy (CIDP). CIDP is thought to be a chronic and more indolent form of the Guillain-Barre Syndrome. The disease progresses either with repeated attacks, called relapses, or in a stepwise or steady fashion. As in GBS, there appears to be destruction of the myelin sheath by antibodies and T-lymphocytes. But since there is no specific test for CIDP, the diagnosis is based on the clinical and laboratory characteristics.

Chronic Polyneuropathies with antibodies to peripheral nerves is still another peripheral demyelinating diseases for which the method of the present inventions can be employed to treat. In some types of chronic neuropathies, antibodies to specific components of nerve have been identified. These include demyelinating peripheral disease associated with antibodies to the Myelin Associated Glycoprotein (MAG), motor neuropathy associated with antibodies to the gangliosides GM1 or GD1a, and sensory neuropathy associated with anti-sulfatide or GD1b ganglioside antibodies. The antibodies in these cases bind to oligosaccharide or sugar like molecules, which are linked to proteins (glycoproteins) or lipids (glycolipids or gangliosides) in the nerves.

The method of the present invention can also be used as part of a therapeutic plan for treating peripheral demyelinating diseases associated with vasculitis or inflammation of the blood vessels in peripheral nerves. Peripheral demyelinating disease can also be caused by Vasculitis—an inflammation of the blood vessels in peripheral nerve. It produces small "strokes" along the course of the peripheral nerves, and may be restricted to the nerves or it may be generalized, include a skin rash, or involve other organs. Several rheumatological diseases like Rheumatoid Arthritis, Lupus, Periarteritis Nodosa, or Sjogren's Syndrome, are associated with generalized Vasculitis, which can also involve the peripheral nerves. Vasculitis can cause Polyneuritis, Mononeuritis, or Mononeuritis Multiplex, depending on the distribution and severity of the lesions.

In some embodiments, the method of the present invention is suitable for the treatment of peripheral demyelinating diseases associated with monoclonal gammopathies. In Monoclonal Gammopathy, single clones of B-cells or plasma cells in the bone marrow or lymphoid organs expand to form benign or malignant tumors and secrete antibodies. "Monoclonal" is because there are single clones of antibodies. And "Gammopathy" stands for gammaglobulins, which is another name for antibodies. In some cases, the antibodies react with nerve components; in others, fragments of the antibodies form amyloid deposits.

In some embodiments, the method of the present invention is suitable for the treatment of peripheral demyelinating diseases associated with tumors or neoplasms. Neuropathy can be due to direct infiltration of nerves by tumor cells or to indirect effect of the tumor. The latter is called Paraneoplastic Neuropathy. Several types have been described. For instance, the method of the present inventions can be used to manage sensory neuropathy associated with lung cancer. Likewise, the method of the present invention can be used to treat peripheral demyelinating diseases associated with multiple myeloma. In some embodiments, the method of the present invention is suitable for the treatment of peripheral demyelinating diseases associated with Waldenstrom's Macroglobulemia, Chronic Lymphocytic Leukemia, or B-cell Lymphoma. In some embodiments, the method of the present invention is used as part of therapeutic protocol for the treatment of patients with cancers where peripheral demyelinating disease is a consequence of local irradiation or be caused by a chemotherapeutic agent. Chemotherapeutic agents known to cause sensory and/or motor neuropathies include vincristine, an antineoplastic drug used to treat haematological malignancies and sarcomas, as well as cisplatin, taxol and others. The neurotoxicity is dose-related, and exhibits as reduced intestinal motility and peripheral neuropathy, especially in the distal muscles of the hands and feet, postural hypotension, and atony of the urinary bladder. Similar problems have been documented with taxol and cisplatin (MoUman, J. E., 1990, New Eng Jour Med. 322: 126-127), although cisplatin-related neurotoxicity can be alleviated with nerve growth factor (NGF) (Apfel, S. C. et al, 1992, Annals of Neurology 31:76-80). Although the neurotoxicity is sometimes reversible after removal of the neuro toxic agent, recovery can be a very slow process (Legha, S., 1986, Medical Toxicology 1:421-427; Olesen, et al, 1991, Drug Safety 6:302-314). In some embodiments, the method of the present invention is particularly suitable for the treatment of peripheral demyelinating diseases induced by inhibitor of the proteasome such as bortezomib. Bortezomib, chemical name: [(1R)-3-methyl-1_ [[(2S)-1-oxo-3-phenyl-2_ [(pyrazin-carboxy) amino] propyl] amino] butyl] boronic acid, was the first to enter the clinical application of proteasome inhibitor, is currently approved by the FDA recommended for multiple myeloma (MM) and mantle cell lymphoma.

In some embodiments, the method of the present invention is suitable for the treatment of peripheral demyelinating diseases caused by infections. Peripheral demyelinating diseases can be caused by infection of the peripheral nerves. Viruses that cause peripheral demyelinating diseases include the AIDS virus, HIV-I, which causes slowly progressive sensory neuropathy, Cytomegalovirus which causes a rapidly progressive paralytic neuropathy, Herpes Zoster which cause Shingles, and Poliovirus which causes a motor neuropathy. Hepatitis B or C infections are sometimes associated with vasculitic neuropathy. Bacterial infections that cause neuropathy include Leprosy which causes a patchy sensory neuropathy, and Diphtheria which can cause a rapidly progressive paralytic neuropathy. Other infectious diseases that cause neuropathy include Lyme disease which is caused by a spirochete, and Trypanosomiasis which is caused by a parasite. Both commonly present with a multifocal neuropathy In some embodiments, the method of the present invention is suitable for the treatment of peripheral demyelinating diseases caused by nutritional imbalance. Deficiencies of Vitamins B12, B1 (thiamine), B6 (pyridoxine), or E, for example, can produce polyneuropathies with degeneration of peripheral nerve axons. This can be due to poor diet, or inability to absorb the nutrients from the stomach or gut. Moreover megadoses of Vitamin B6 can also cause a peripheral demyelinating disease, and the method of the present invention can be used as part of a de-toxification program in such cases.

In some embodiments, the method of the present invention is suitable for the treatment of peripheral demyelinating diseases arising in kidney diseases. Chronic renal failure can cause a predominantly sensory peripheral neuropathy with degeneration of peripheral nerve axons.

In some embodiments, the method of the present invention is suitable for the treatment of hypothyroid neuropathies. Hypothyroidism is sometimes associated with a painful sensory polyneuropathy with axonal degeneration. Mononeuropathy or Mononeuropathy Multiplex can also occur due to compression of the peripheral nerves by swollen tissues.

In some embodiments, the method of the present invention is suitable for the treatment of peripheral demyelinating diseases caused by Alcohol and Toxins. Certain toxins can cause Peripheral Neuropathy. Lead toxicity is associated with a motor neuropathy; arsenic or mercury cause a sensory neuropathy, Thalium can cause a sensory and autonomic neuropathy, several of the organic solvents and insecticides can also cause polyneuropathy. Alcohol is directly toxic to nerves and alcohol abuse is a major cause of neuropathy. The method of the present invention can be used, in some embodiments, as part of a broader detoxification program. In still another embodiment, the method of the present invention can be used for the treatment of peripheral demyelinating diseases caused by drugs. Several drugs are known to cause neuropathy. They include, among others, nitrofurantoin, which is used in pyelonephritis, amiodarone in cardiac arrhythmias, disulfiram in alcoholism, ddC and ddl in AIDS, and dapsone which is used to treat Leprosy. As above, the method of the present invention can be used, in some embodiments, as part of a broader detoxification program.

In some embodiments, the method of the present invention is suitable for the treatment of peripheral demyelinating diseases caused by trauma or compression. Localized neuropathies can result from compression of nerves by external pressure or overlying tendons and other tissues. The best known of these are the Carpal Tunnel Syndrome which results from compression at the wrist, and cervical or lumbar radiculopathies (Sciatica) which result from compression of nerve roots as they exit the spine. Other common areas of nerve compression include the elbows, armpits, and the back of the knees.

The method of the present invention is also useful in variety of idiopathic peripheral demyelinating diseases. The term "idiopathic" is used whenever the cause of the peripheral demyelinating disease cannot be found. In these cases, the peripheral demyelinating disease is classified according to its manifestations, i.e., sensory, motor, or sensorimotor idiopathic polyneuropathy.

As used herein the expression "polynucleotide of interest" herein designates any nucleotide sequence coding for any polypeptide, structural protein, enzyme etc., the expression of which is wanted in a target cell, for any kind of reason. It can also designate a non-coding sequence, for example an antisense sequence or the sequence of an interfering RNA aimed at decreasing the expression of a gene. One skilled in the art knows, by its knowledge of the scientific literature in his field, which are the polynucleotides that may be more appropriate to treat a specific disease affecting the peripheral nervous system. Gene therapy of the peripheral nervous system with the AAV9 vectors of the present invention can be performed either by e.g. introducing in Schwann cells a functional copy of a polynucleotide of interest (e.g. a gene) that is deficient therein (gene replacement therapy), or by delivering to Schwann cells a polynucleotide of interest which will have a beneficial effect on the disease to be treated (symptomatic therapy). In particular the polynucleotide product leads to the expression of a polypeptide that will enhance the function of target cells (e.g. Schwann cells). Examples of polynucleotides of interest that can be used for gene replacement therapy are genes that are specifically or preferentially expressed by deficient Schwann cells. In some embodiments, the polynucleotide of interest may encode for a neurotrophic factor. As used herein, the "neurotrophic factor" is a generic term of proteins having a physiological action such as survival and maintenance of nerve cells, promotion of neuronal differentiation. Examples of neurotrophic factors include but are not limited to bFGF, aFGF, BDNF, CNTF, IL-1beta, NT-3, IGF-II, GDNF, and NGF. In some embodiments, the polynucleotide of interest encodes for a dominant negative mutant. A dominant negative mutant is a polypeptide or a nucleic acid coding region sequence which has been changed with regard to at least one position in the sequence, relative to the corresponding wild type native version at a position which changes an amino acid residue position at an active site required for biological activity of the native polypeptide. For example, a dominant negative mutant may consist of a truncated polypeptide that may act as a competitive inhibitor of the native polypeptide. In some embodiments, the polynucleotide product of interest is a site-specific endonuclease that provides for site-specific knock-down of gene function, e.g., where the endonuclease knocks out an allele associated with a peripheral nerves disease. For example, where a dominant allele encodes a defective copy of a gene that, when wild-type, is a myelin protein and/or provides for normal Schwann cell function, a site-specific endonuclease (such as TALE nucleases, meganucleases, Zinc finger nucleases, and CRISPR/Cas9 constructs) can be targeted to the defective allele and knock out the defective allele. In addition to knocking out a defective allele, a site-specific nuclease can also be used to stimulate homologous recombination with a donor DNA that encodes a functional copy of the protein encoded by the defective allele. Thus, for example, the method of the invention can be used to deliver both a site-specific endonuclease that knocks out a defective allele, and can be used to deliver a functional copy of the defective allele, resulting in repair of the defective allele, thereby providing for production of a functional protein. In some embodiments, the vector comprises a polynucleotide that encodes a site-specific endonuclease; and a polynucleotide that encodes a functional copy of a defective allele, where the functional copy encodes a functional protein. Site-specific endonucleases that are suitable for use include, e.g., zinc finger nucleases (ZFNs); and transcription activator-like effector nucleases (TALENs), where such site-specific endonucleases are non-naturally occurring and are modified to target a specific gene. Such site-specific nucleases can be engineered to cut specific locations within a genome, and nonhomologous end joining can then repair the break while inserting or deleting several nucleotides. Such site-specific endonucleases (also referred to as "INDELs") then throw the protein out of frame and effectively knock out the gene. See, e.g., U.S. Patent Publication No. 2011/0301073. In some embodiments, the polynucleotide of interest is an antisense oligonucleotide constructs. Anti-sense oligonucleotides, including anti-sense RNA molecules and anti-sense DNA molecules, would act to directly block the translation of the targeted mRNA by binding thereto and thus preventing protein translation or increasing mRNA degradation, thus decreasing the level of the targeted protein, and thus activity, in a cell. In some embodiments, the polynucleotide of interest is a siRNA. Small inhibitory RNAs (siRNAs) can also function as inhibitors of gene expression for use in the present invention. Gene expression can be reduced by contacting the tumor, subject or cell with a small double stranded RNA (dsRNA), or a vector or construct causing the production of a small double stranded RNA, such that gene expression is specifically inhibited (i.e. RNA interference or RNAi). In some embodiments, the polynucleotide of interest is a ribozyme. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of the targeted mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays. In some embodiments, the polynucleotide of interest is an antagomir. As used herein an "antagomir" is a nucleic acid oligomer that is designed to bind to a specific target microRNA via complementary base pairing (for example, as described above). An antagomir may have a sequence that is wholly or partially complementary to the target microRNA sequence. Antagomirs may have a single stranded, double stranded, partially double-stranded, or hairpin structure. Antagomirs may further comprise chemically modified nucleotides (e.g. as described below). In some embodiments, the polynucleotide of interest is a microRNA sponge. As used herein, the term "microRNA-sponge" is a nucleic acid that comprises multiple (e.g. at least 2, 3, 4, 5 or 6) binding sites for a specific target microRNA. Thus, a microRNA-sponge is able to bind and sequester multiple target microRNA molecules. A microRNA sponge may comprise an mRNA expressed from a vector (e.g. a viral vector or plasmid vector). The presence in a microRNA-sponge of multiple binding sites for the target microRNA enables microRNAs to be adsorbed in a manner analogous to a sponge soaking up water. A microRNA-sponge may bind target microRNAs via complementary base pairing (for example, as described above).

As used herein the term "AAV9 vector" has its general meanings in the art and refers to a vector derived from an adeno-associated virus serotype 9. In particular, the term "AAV9", as used herein, refers to a serotype of adeno-associated virus with a genome sequence as defined in the GenBank accession number AAS99264. The AAV9 vector of the present invention can have one or more of the AAV9 wild-type genes deleted in whole or part, preferably the rep and/or cap genes, but retain functional flanking ITR sequences. Functional ITR sequences are necessary for the rescue, replication and packaging of the AAV virion. Thus, an AAV9 vector is defined herein to include at least those sequences required in cis for replication and packaging (e.g., functional ITRs) of the virus. The ITRs need not be the wild-type nucleotide sequences, and may be altered, e.g by the insertion, deletion or substitution of nucleotides, so long as the sequences provide for functional rescue, replication and packaging. AAV9 expression vectors are constructed using known techniques to at least provide as operatively linked components in the direction of transcription, control elements including a transcriptional initiation region, the polynucleotide of interest and a transcriptional termination region. The control elements are selected to be functional in a mammalian cell. The resulting construct which contains the operatively linked components is bounded (5' and 3') with functional AAV9 ITR sequences. By "adeno-associated virus inverted terminal repeats" or "AAV9 ITRs" is meant the art-recognized regions found at each end of the AAV genome which function together in cis as origins of DNA replication and as packaging signals for the virus. AAV9 ITRs, together with the AAV9 rep coding region, provide for the efficient excision and rescue from, and integration of a nucleotide sequence interposed between two flanking ITRs into a mammalian cell genome.

The AAV9 vector of the present invention can be constructed by directly inserting the selected sequence (s) into an AAV9 genome which has had the major AAV9 open reading frames ("ORFs") excised therefrom. Other portions of the AAV9 genome can also be deleted, so long as a sufficient portion of the ITRs remain to allow for replication and packaging functions. Such constructs can be designed using techniques well known in the art. See, e.g. U.S. Pat. Nos. 5,173,414 and 5,139,941; International Publications Nos. WO 92/01070 (published 23 Jan. 1992) and WO 93/03769 (published 4 Mar. 1993); Lebkowski et al., 1988; Vincent et al., 1990; Carter, 1992; Muzyczka, 1992; Kotin, 1994; Shelling and Smith, 1994; and Zhou et al., 1994. Alternatively, AAV ITRs can be excised from the viral genome or from an AAV vector containing the same and fused 5' and 3' of a selected nucleic acid construct that is present in another vector using standard ligation techniques. AAV9 vectors which contain ITRs have been described in, e.g. U.S. Pat. No. 5,139,941. In particular, several AAV vectors are described therein which are available from the American Type Culture Collection ("ATCC") under Accession Numbers 53222, 53223, 53224, 53225 and 53226. Additionally, chimeric genes can be produced synthetically to include AAV9 ITR sequences arranged 5' and 3' of one or more selected nucleic acid sequences. Preferred codons for expression of the chimeric gene sequence in mammalian PNS cells can be used. The complete chimeric sequence is assembled from overlapping oligonucleotides prepared by standard methods. See, e.g., Edge, 1981; Nambair et al., 1984; Jay et al., 1984. In order to produce AAV virions, an AAV expression vector is introduced into a suitable host cell using known techniques, such as by transfection. A number of transfection techniques are generally known in the art. See, e.g., Graham et al., 1973; Sambrook et al. (1989) Molecular Cloning, a laboratory manual, Cold Spring Harbor Laboratories, New York, Davis et al. (1986) Basic Methods in Molecular Biology, Elsevier, and Chu et al., 1981. Particularly suitable transfection methods include calcium phosphate co-precipitation (Graham et al., 1973), direct microinjection into cultured cells (Capecchi, 1980), electroporation (Shigekawa et al., 1988), liposome mediated gene transfer (Mannino et al., 1988), lipid-mediated transduction (Felgner et al., 1987), and nucleic acid delivery using high-velocity microprojectiles (Klein et al., 1987).

Typically the AAV9 vector of the present invention comprises an expression cassette. The term "expression cassette", as used herein, refers to a nucleic acid construct comprising nucleic acid elements sufficient for the expression of the polynucleotide of interest. Typically, an expression cassette comprises the polynucleotide of interest operatively linked to a promoter sequence. The term "operatively linked" refers to the association of two or more nucleic acid fragments on a single nucleic acid fragment so that the function of one is affected by the other. For example, a promoter is operatively linked with a coding sequence when it is capable of affecting the expression of that coding sequence (e.g., the coding sequence is under the transcriptional control of the promoter). Encoding sequences can be operatively linked to regulatory sequences in sense or antisense orientation. In some embodiments, the promoter is a heterologous promoter. The term "heterologous promoter", as used herein, refers to a promoter that does is not found to be operatively linked to a given encoding sequence in nature. In some embodiments, an expression cassette may comprise additional elements, for example, an intron, an enhancer, a polyadenylation site, a woodchuck response element (WRE), and/or other elements known to affect expression levels of the encoding sequence. As used herein, the term "promoter", as used herein, refers to a nucleotide sequence capable of controlling the expression of a coding sequence or functional RNA. In general, the polynucleotide of interest is located 3' of a promoter sequence. In some embodiments, a promoter sequence consists of proximal and more distal upstream elements and can comprise an enhancer element. An "enhancer" is a nucleotide sequence that can stimulate promoter activity and may be an innate element of the promoter or a heterologous element inserted to enhance the level or tissue-specificity of a promoter. In some embodiments, the promoter is derived in its entirety from a native gene. In some embodiments, the promoter is composed of different elements derived from different naturally occurring promoters. In some embodiments, the promoter comprises a synthetic nucleotide sequence. It will be understood by those skilled in the art that different promoters will direct the expression of a gene in different tissues or cell types, or at different stages of development, or in response to different environmental conditions or to the presence or the absence of a drug or transcriptional co-factor. Ubiquitous, cell-type-specific, tissue-specific, developmental stage-specific, and conditional promoters, for example, drug-responsive promoters (e.g. tetracycline-responsive promoters) are well known to those of skill in the art. Examples of promoter include, but are not limited to, the phophoglycerate kinase (PKG) promoter, CAG, NSE (neuronal specific enolase), synapsin or NeuN promoters, the SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), SFFV promoter, rous sarcoma virus (RSV) promoter, synthetic promoters, hybrid promoters, and the like. The promoters can be of human origin or from other species, including from mice. In addition, sequences derived from nonviral genes, such as the murine metallothionein gene, will also find use herein. Such promoter sequences are commercially available from, e.g. Stratagene (San Diego, Calif.). In some embodiments, the expression cassette comprises an appropriate secretory signal sequence that will allow the secretion of the polypeptide encoded by the polynucleotide of interest. As used herein, the term "secretory signal sequence" or variations thereof are intended to refer to amino acid sequences that function to enhance (as defined above) secretion of an operably linked polypeptide from the cell as compared with the level of secretion seen with the native polypeptide. As defined above, by "enhanced" secretion, it is meant that the relative proportion of the polypeptide synthesized by the cell that is secreted from the cell is increased; it is not necessary that the absolute amount of secreted protein is also increased. In some embodiments, essentially all (i.e., at least 95%, 97%, 98%, 99% or more) of the polypeptide is secreted. It is not necessary, however, that essentially all or even most of the polypeptide is secreted, as long as the level of secretion is enhanced as compared with the native polypeptide. Generally, secretory signal sequences are cleaved within the endoplasmic reticulum and, in some embodiments, the secretory signal sequence is cleaved prior to secretion. It is not necessary, however, that the secretory signal sequence is cleaved as long as secretion of the polypeptide from the cell is enhanced and the polypeptide is functional. Thus, in some embodiments, the secretory signal sequence is partially or entirely retained. The secretory signal sequence can be derived in whole or in part from the secretory signal of a secreted polypeptide (i.e., from the precursor) and/or can be in whole or in part synthetic. The length of the secretory signal sequence is not critical; generally, known secretory signal sequences are from about 10-15 to 50-60 amino acids in length. Further, known secretory signals from secreted polypeptides can be altered or modified (e.g., by substitution, deletion, truncation or insertion of amino acids) as long as the resulting secretory signal sequence functions to enhance secretion of an operably linked polypeptide. The secretory signal sequences of the invention can comprise, consist essentially of or consist of a naturally occurring secretory signal sequence or a modification thereof (as described above). Numerous secreted proteins and sequences that direct secretion from the cell are known in the art. The secretory signal sequence of the invention can further be in whole or in part synthetic or artificial. Synthetic or artificial secretory signal peptides are known in the art, see e.g., Barash et al., "Human secretory signal peptide description by hidden Markov model and generation of a strong artificial signal peptide for secreted protein expression," Biochem. Biophys. Res. Comm 294:835-42 (2002); the disclosure of which is incorporated herein in its entirety.

Administering the vector of the invention may be done by direct injection into the nerve. The doses of vectors may be adapted depending on the disease condition, the subject (for example, according to his weight, metabolism, etc.), the treatment schedule, etc. A preferred effective dose within the context of this invention is a dose allowing an optimal transduction of the Schwann cells. Typically, from $10^8$ to $10^{10}$ viral genomes (vg) are administered per dose in mice. Typically, the doses of AAV9 vectors to be administered in humans may range from $10^{10}$ to $10^{12}$ vg.

The AVV9 vector of the present invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient (i.e. the vector of the invention). The precise nature of the carrier or other material may be determined by the skilled person according to the route of administration. The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. For injection, the active ingredient will be in the form of an aqueous solution, which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. For delayed release, the vector may be included in a pharmaceutical composition, which is formulated for slow release, such as in microcapsules formed from biocompatible polymers or in liposomal carrier systems according to methods known in the art.

The invention will be further illustrated by the following figures and examples. However, these examples and figures should not be interpreted in any way as limiting the scope of the present invention.

FIGURES

FIG. 1: Cryosection analysis on OCT-embedded adult mice sciatic nerves showing the transduction profile of AAV-injected sciatic nerves. Whole sciatic nerve is represented in the first lane, zoom at ×20 is represented in the second lane.

FIG. 2: Percentage of myelinating Schwann cells transduced among all the myelinating Schwann cells along the AAV9-injected PNH sciatic nerve. Analysis were performed on OCT and paraffin-embedded sciatic nerve sections.

EXAMPLE 1: INTRASCIATIC INJECTION ON ADULT MICE

Methods:

The methodology of injection is described in the following publication (Gonzalez et al., 2014) with the parameters below. Briefly, mice were anaesthetized with isoflurane, and were maintained under isoflurane during the surgery. Incision was made with a scalpel at the mid-thigh; sciatic nerve was lifted out with spatula and exposed. The vectors were co-injected into the sciatic nerve with Fast green (0.005% final concentration) via glass needles, at <45° acute angle to the nerve surface, connected to a micro injector linked to a pulse generator. The capillary remained in place at the injection site for 1 additional min, before it was slowly removed. The injection parameters are listed in the table below.

TABLE 1

| injection parameters on adult mice | |
|---|---|
| Vectors | AAV9 and AAVrh10_CAG_eGFP |
| Injection | Unilateral in the right sciatic nerve |
| Quantity of vector per nerve | $4.6 \times 10^{10}$ gc/nerve |
| Volume injected per nerve | 8 µl |
| Injection time | 15 min |
| Number of mice per vectors | 9 |
| Age of injection | 2 months |
| Sacrifice | 1 month post injection |

Results

To explore the ability of AAV vector to transduce axons or Schwann cells, we performed teasing analysis on injected sciatic nerves (three injected nerves per vector). Thus, among all the transduced cells, we determined the percentage of transduced myelinating Schwann cells, non-myelinating Schwann cells and axons (Table 2).

TABLE 2

Teasing analysis of AAV-injected mice sciatic nerves showing the ability of AAV vector to transduce axons or Schwann cells. The results are presented as a percentage of axons or myelinating Schwann cells or non myelinating Schwann cells transduced among all the transduced cells.

| | AAV9-CAG-eGFP (N = 3) | | AAV10-CAG-eGFP (N = 3) | |
|---|---|---|---|---|
| | Mean (%) | SD (%) | Mean (%) | SD (%) |
| Myelinating Schwann cells | 97 | 4 | 82 | 17 |
| Non myelinating Schwann cells | 3 | 3 | 4 | 4 |
| Axons | 0 | 0 | 14 | 13 |

AAV9 transduced almost exclusively myelinating Schwann cells (97%), very few non myelinating Schwann (3%) cells and no axons. AAVrh10 shows a transduction profile slightly different with a strong proportion of myelinating Schwann cells (82%), very few non myelinating Schwann cells (4%) and some axons (14%)

In parallel to teasing analysis, coronal sections of OCT-embedded sciatic nerves were performed (four injected sciatic nerves per vector). The profile of transduction obtained for each vector in a whole coronal section of the sciatic nerve at the injection site is described in FIG. 1. AAV9 clearly displayed a higher rate of transduction than AAVrh10. To determine the types of transduced cells, coronal sections of sciatic nerve were stained either for MBP, a myelinating Schwann cell marker, or for TUJ1, an axonal cell marker. We found that AAV9 and AAVrh10 expression were mostly detected in myelinating Schwann cells. At the injection site, up to 93% of positive myelinating Schwann cells were counted with AAV9, whereas only 51% with AAVrh10. Moreover, along the sciatic nerve, AAV9 displayed a better diffusion than AAVrh10, with respectively 63 and 42% at 1 cm proximal from the injection site, 91 and 42% at 1 cm distal from the injection site (Table 3).

TABLE 3

Percentage of myelinating Schwann cells transduced among all the myelinating Schwann cells along the AAV-injected mice sciatic nerves.

| | AAV9-CAG-eGFP (N = 3) | | AAV10-CAG-eGFP (N = 3) | |
|---|---|---|---|---|
| | Mean (%) | SD (%) | Mean (%) | SD (%) |
| 1 cm proximal from the Injection site | 63 | 24 | 42 | 22 |
| Injection site | 93 | 2 | 51 | 11 |
| 1 cm distal from the injection site | 91 | 2 | 42 | 16 |

Moreover, vector genome copy (VGC) from entire sciatic nerve for each group of injected adult mice (three mice per vector) was evaluated. First, DNA extraction was performed thanks to DNA blood and tissue kit (Qiagen) by following the manufacturer instructions. Then, qPCR was realized using two different primers, one against eGFP transgene and one against ITR sequence. The results are presented in table 4.

TABLE 4

VGC evaluated by qPCR on DNA extracted from the entire sciatic nerve using either primers against eGFP transgene or primers against ITR sequence.

| | | AAV9-CAG-eGFP (N = 3) | | AAV10-CAG-eGFP (N = 3) | |
|---|---|---|---|---|---|
| | | Mean | SD | Mean | SD |
| VGC | eGFP | 0.551 | 0.146 | 0.525 | 0.084 |
| | ITR | 0.507 | 0.077 | 0.338 | 0.113 |

The results showed the ability of AAV vector to transduce mouse sciatic nerve with roughly a similar pattern for AAV9 and AAVrh10 with VGC around 0.5.

EXAMPLE 2: INTRASCIATIC INJECTION ON PUPS MICE (P3-P4)

Methods:

The same methodology of injection described in the example 1 was used with the following parameters (Table 5):

TABLE 5

| injection parameters in pups' mice | |
|---|---|
| Vectors | AAV9-CAG-eGFP |
| Injection | Unilateral in the right sciatic nerve |
| Quantity of vector per nerve | $1.15 \times 10^{10}$ gc/nerve |
| Volume injected per nerve | 2 µl |
| Injection time | 3-4 min |
| Number of mice per vectors | 7 |
| Age of injection | P3-P4 |
| Sacrifice | 1 month post injection |

Results

To explore the ability of AAV vector to transduce axons or Schwann cells, we performed teasing analysis on injected sciatic nerves (three pups' mice). Teasing results are presented in the Table 6.

TABLE 6

Teasing analysis of AAV-injected mice sciatic nerves showing the ability of AAV vector to transduce axons or Schwann cells. The results are presented as a percentage of axons or myelinating Schwann cells or non-myelinating Schwann cells transduced among all the transduced cells.

|  | AAV9-CAG-eGFP (N = 3) | |
|---|---|---|
|  | Mean (%) | SD (%) |
| Myelinating Schwann cells | 87 | 12 |
| Non myelinating Schwann cells | 2 | 2 |
| Axons | 14 | 12 |

In pups mice, AAV9 transduced almost exclusively myelinating Schwann cells (87%), few non myelinating Schwann (14%) cells and very few axons (2%).

In parallel to teasing analysis, coronal sections of OCT-embedded sciatic nerves were performed (three injected mice), as described in the example 1. On the injection site, up to 84% of positive myelinating Schwann cells were counted. At 1 cm proximal from the injection site, 74% of myelinating Schwann cells were transduced and at 1 cm distal from the injection site, 74% of myelinating Schwann cells were transduced (Table 7).

TABLE 7

Percentage of myelinating Schwann cells transduced among all the myelinating Schwann cells along the AAV-injected pups' mice sciatic nerves.

|  | AAV9-CAG-eGFP (N = 3) | |
|---|---|---|
|  | Mean (%) | SD (%) |
| 1 cm proximal from the Injection site | 74 | 7 |
| Injection site | 85 | 15 |
| 1 cm distal from the injection site | 74 | 14 |

EXAMPLE 3: INTRASCIATIC INJECTION ON RATS

Methods:

The same methodology of injection described before was used with the following parameters (Table 8):

TABLE 8 injection parameters in rats

| Vectors | AAV9_CAG_eGFP |
|---|---|
| Injection | Unilateral in the right sciatic nerve |
| Quantity of vector per nerve | $1.8 \times 10^{11}$ gc/nerve |
| Volume injected per nerve | 30 µl |
| Injection time | 15 min |
| Number of mice per vectors | 7 |
| Age of injection | 1 month |
| Sacrifice | 1 month post injection |

Results

Teasing analysis (three injected rats) and coronal sections of OCT-embedded sciatic nerves (three injected rats) were performed. The results are presented below (Table 9).

TABLE 9

Teasing analysis of AAV-injected mice sciatic nerves showing the ability of AAV vector to transduce axons or Schwann cells. The results are presented as a percentage of axons or myelinating Schwann cells or non- myelinating Schwann cells transduced among all the transduced cells.

|  | AAV9-CAG-eGFP (N = 3) | |
|---|---|---|
|  | Mean (%) | SD (%) |
| Myelinating Schwann cells | 89 | 9 |
| Non myelinating Schwann cells | 7 | 5 |
| Axons | 4 | 4 |

In rats, AAV9 transduced almost exclusively myelinating Schwann cells (89%), very few non myelinating Schwann (7%) cells and very few axons (4%).

In parallel to teasing analysis, coronal sections of OCT-embedded sciatic nerves were performed (three injected rats), as described before. Along all the nerve, up to 80% of myelinating Schwann cells were transduced (Table 10).

TABLE 10

Percentage of myelinating Schwann cells transduced among all the myelinating Schwann cells along the AAV-injected rat sciatic nerves.

|  | AAV9-CAG-eGFP (N = 3) | |
|---|---|---|
|  | Mean (%) | SD (%) |
| Among all the nerve | 80 | 14 |

EXAMPLE 4: INTRASCIATIC INJECTION ON NON-HUMAN PRIMATE (NHP)

Methods

Anaesthetized NHP are placed in a ventral decubitus prone position. After sciatic nerve exposure, the vector was co-injected with fast green (0.005% final concentration) into the left tibial nerve 1cm above the bifurcation between the common fibular nerve and the tibial nerve. First, a 22 gauge needle is inserted into the epineurium (4 mm) and then a silica capillary, containing the vector and connected to a micropump, is pulled up through the needle. The capillary remained in place on the injection site for 1-2 additional min, before it was slowly removed. The injection parameters are listed in the table below (Table 11).

TABLE 11

Injection parameters in non-human primate

| Vectors | AAV9_CAG_eGFP | AAVrh10_CAG_eGFP |
|---|---|---|
| Injection | Unilateral in the left sciatic nerve | |
| Quantity of vector per nerve | $5 \times 10^{12}$ gc/nerve | $5 \times 10^{12}$ gc/nerve |
| Volume injected per nerve | 400 µl | 400 µl |
| Injection time | 30 min | 30 min |
| Number of NHP per vectors | 1 | 1 |
| Age of injection | 2 years | 2 years |
| Sacrifice | 1 month post injection | 1 month post injection |

Results:

Similarly to the AAV-injected mice, we analyzed the profile of transduction and the types of transduced cells.

Immunostaining on coronal sections of OCT-embedded sciatic nerve showed that AAV9-driven expression was seen exclusively in myelinating Schwann cells and not in axons (FIG. 2). On NHP, only myelinating Schwann cells are transduced and no axons are transduced. The AAV9 GFP expression was detected along the sciatic nerve in a total distance of 5.5 cm, more precisely 3.5 cm proximal from the injection site and 1.5 cm distal from the injection with respectively 20 and 70% of transduced myelinating Schwann cells (FIG. 2). Up to 70% of positive myelinating Schwann cells were found on the injection site. This percentage decreased with the proximal distance from the injection site and was constant up to 1.5 cm distal from the injection site (FIG. 2). These results were confirmed by paraffin-embedded sciatic nerve sections

CONCLUSION

Intrasciatic injection of AAV9 on mice (pups and adults), rats and non-human primate showed a strong transduction rate of myelinating Schwann cells with a good diffusion of the vector, never obtained and described in the literature up to now. These results highlight that AAV9 vector could represent a useful therapeutic tool to express proteins mutated or deregulated in myelinating Schwann cells in pathologies affecting the peripheral nervous system.

REFERENCES

Throughout this application, various references describe the state of the art to which this invention pertains. The disclosures of these references are hereby incorporated by reference into the present disclosure.

The invention claimed is:

1. A method for expressing a polynucleotide in myelinating Schwann cells of a subject with a peripheral demyelinating disease, comprising
    injecting an AAV9 vector that encodes the polynucleotide into a peripheral nerve of the subject, wherein the AAV9 vector preferentially transduces the myelinating Schwann cells over non-myelinating Schwann cells along the peripheral nerve, and wherein the polynucleotide is expressed in transduced myelinating Schwann cells along the peripheral nerve.

2. The method of claim 1, wherein the peripheral demyelinating disease is selected from the group consisting of hereditary peripheral demyelinating diseases and acquired peripheral demyelinating diseases.

3. The method of claim 1, wherein the peripheral demyelinating disease is selected from the group consisting of Refsum's disease, Abetalipoproteinemia, Tangier disease, Krabbe's disease, Metachromatic leukodystrophy, Fabry's disease, Dejerine-Sottas syndrome, and Charcot-Marie-Tooth Diseases.

4. The method of claim 1, wherein the peripheral demyelinating disease is selected from the group consisting of diabetic neuropathies, immune-mediated neuropathies, acute motor neuropathy, acute sensory neuropathy, acute autonomic neuropathy, chronic polyneuropathies, peripheral demyelinating diseases associated with vasculitis or inflammation of the blood vessels in peripheral nerves, peripheral demyelinating diseases associated with monoclonal gammopathies, peripheral demyelinating diseases associated with tumors or neoplasms, peripheral demyelinating diseases caused by infections, peripheral demyelinating diseases caused by nutritional imbalance, peripheral demyelinating diseases arising in kidney diseases, hypothyroid neuropathies, peripheral demyelinating diseases caused by alcohol and toxins, peripheral demyelinating diseases caused by trauma or compression, and idiopathic peripheral demyelinating diseases.

5. The method of claim 1, wherein the polynucleotide is an antisense oligonucleotide construct.

6. The method of claim 1, wherein the polynucleotide is a siRNA.

7. The method of claim 1, wherein the polynucleotide is operatively linked to a promoter sequence.

8. The method of claim 1, wherein the AAV9 vector does not transduce axons.

9. The method of claim 1, wherein about 97% of the myelinating Schwann cells are transduced.

10. The method of claim 1, wherein the subject is a primate.

* * * * *